(12) United States Patent
Sutton (10) Patent No.: US 6,693,445 B1
(45) Date of Patent: Feb. 17, 2004

(54) PROBE DEVICE FOR APPARATUS FOR MONITORING CORROSION OF A MATERIAL

(76) Inventor: John Sutton, The Willows, Mid Holmwood Lane, Dorking, Surrey RH5, 4HA (GB)

( * ) Notice: Subject to any disclaimer, the term of this patent is extended or adjusted under 35 U.S.C. 154(b) by 0 days.

(21) Appl. No.: 09/936,021

(22) Filed: Dec. 10, 2001

Related U.S. Application Data

(60) Provisional application No. PCT/GB00/00828, filed on Mar. 7, 2000.

(30) Foreign Application Priority Data

Mar. 8, 1999 (GB) ............................................. 9905274

(51) Int. Cl.⁷ ............................................. G01R 27/08
(52) U.S. Cl. ....................................... 324/700; 324/706
(58) Field of Search .................................. 324/700, 706

(56) References Cited

U.S. PATENT DOCUMENTS

| | | | |
|---|---|---|---|
| 3,124,771 A | 3/1964 | Rohrback | |
| 3,821,642 A | 6/1974 | Seymour | 324/65 CR |
| 4,019,133 A | 4/1977 | Manley et al. | 324/65 CR |
| 4,338,097 A | * 7/1982 | Turner et al. | 436/6 |
| 4,338,563 A | 7/1982 | Rhoades et al. | 324/65 CR |
| 4,703,254 A | 10/1987 | Strommen | 324/65 CR |
| 4,755,744 A | * 7/1988 | Moore et al. | 324/700 |
| 5,036,287 A | 7/1991 | Serwatzky | 324/700 |
| 5,332,961 A | 7/1994 | Hammerle | 324/700 |
| 5,351,003 A | 9/1994 | Bauer et al. | 324/207.12 |
| 5,583,426 A | 12/1996 | Tiefnig | 324/71.2 |

FOREIGN PATENT DOCUMENTS

| | | |
|---|---|---|
| EP | 0 039 750 | 11/1981 |
| EP | 0 150 552 B2 | 12/1992 |
| GB | 2 064 124 A | 6/1981 |
| GB | 2 081 904 A | 2/1982 |
| GB | 0 150 552 A1 | 8/1985 |
| GB | 2 158 246 A | 11/1985 |
| GB | 2 180 068 A | 3/1987 |
| GB | 2 262 608 A | 6/1993 |
| GB | 2 266 379 A | 10/1993 |

OTHER PUBLICATIONS

"Corrosion–Indicating Device", IBM Technical Disclosure Bulletin, US, IBM Corp., New York, vol. 32, No. 10A, Mar. 1, 1990, p. 25.

* cited by examiner

Primary Examiner—N. Le
Assistant Examiner—John Teresinski
(74) Attorney, Agent, or Firm—Westman, Champlin & Kelly (57) ABSTRACT

A probe is disclosed which is suitable for use with an apparatus for monitoring the corrosion of a material by accurately measuring changes in the resistance of an exposed element (101) in relation to a reference element (103). The two elements are electrically connected in series via a bridge (131). The elements are formed from the same piece of material divided along an elongate slot (167) and are proximate to one another so that the temperature difference between them is kept to a minimum. This prevents false indications of corrosion by ensuring that the temperature coefficient of the resistivities is the same in both elements. The reference element (103) is covered with a corrosion-resistant layer. (113). This layer (113) is preferably as thin as possible and also a good thermal conductor to further ensure equal temperature of the reference (103) and exposed (101) elements.

19 Claims, 4 Drawing Sheets

PROBE DEVICE FOR APPARATUS FOR MONITORING CORROSION OF A MATERIAL

The present application is a Section 371 Application and claims priority under 35 U.S.C. § 119 of International patent application Serial No. PCT/GB00/00828, filed Mar. 7, 2000, and published in English the content of which is hereby incorporated by reference in its entirety.

FIELD OF THE INVENTION

The present invention relates to electrical resistance corrosion monitors for detecting loss of material due to corrosion and/or erosion caused by the interaction of that material with its environment. More specifically, the present invention relates to probe devices for electrical corrosion monitors.

DISCUSSION OF THE PRIOR ART

Corrosion monitors are commonly used for detecting and monitoring loss of material due to corrosion and/or erosion caused by the interaction between the material and the environment in contact with the material. Corrosion monitors generally detect the loss of material by an electrical resistance method. Such corrosion monitors typically comprise a probe device that has an element comprising a material that exhibits similar erosion/corrosion susceptibility as the material to be monitored, for example the metal material of the interior surface of steel pipes used in gas and oil pipelines. The element is situated in the same environment, e.g. the pipeline fluid, that is in contact with the metal material, e.g. steel pipe. The resistance of the element increases due to reduction of the cross-sectional area of the element caused by the corrosion and/or erosion of the element by the environment in which the element and metal material are situated. The increase in resistance of the element provides an indication of the corrosion and erosion of the metal material.

Resistance of the element of the metal material in corrosion monitors is commonly monitored by supplying a current through the probe device holding the exposed element and a reference element, where the reference element is protected from and inaccessible by the fluid and in series with the exposed element. The voltages across both elements are measured and the resistance ratio of the exposed element resistance to the reference element resistance is then calculated. The change of resistance ratio is representative of the loss of material of the exposed element. Of course, the sensitivity of the corrosion monitor is dependent on both the current supplied to the elements and the resistance of the elements. Accordingly, the larger the current and/or the larger the resistance values of the elements, the greater the sensitivity of the corrosion monitor.

However, the sensitivity of the corrosion monitor is limited by various factors. For instance, the sensitivity of the corrosion monitor is dependent on the maximum current and the maximum resistance of the element. The environment in which the element is situated is often potentially explosive, such as in gas and oil pipelines. The maximum current in such environments is limited to intrinsic safety requirements. Typically the maximum current permissible is less than 100 mA in such environments and the typical resistance of the element is usually in the range of 1 to 10 mΩ. Higher element resistances, thus higher sensitivities, are attainable with elements having smaller cross-sectional areas, e.g. less than 0.5 mm thick, although, the useful life of such an exposed element is reduced. Accordingly, the sensitivity of corrosion monitors is limited by the relatively small measured resistive voltages which are usually in the range of 10 to 100 $\mu$V. Disturbances such as noise and dc offsets occurring in the electronic circuitry of the corrosion monitor and thermoelectric voltages and electromagnetic noise occurring in the leads between the electronic circuitry and the probe make accurate high resolution measurements of such small voltages difficult.

Additionally, changes in temperature in the environment in which the element is situated changes the resistance of the element. For example, the resistance of steel may change by 0.4% per ° C. Accordingly, in electrical resistance corrosion monitors configured with an exposed element and a reference element, changes in fluid temperatures significantly limits the accuracy and sensitivity of the monitor if the temperature of the exposed element and reference element differ.

In the prior art designs, different values of temperature coefficients of resistivities of the elements limits the performance of the corrosion monitor. Even if the temperature coefficient of resistivity values differ as little as 10 ppm ° C.$^{-1}$, a change in probe temperature of 50° C. causes a change in the resistance ratio by 500 ppm, giving a false indication of corrosion. Hence, the accuracy and sensitivity of such prior art electrical resistance corrosion monitors is limited to detect corrosion in days or months. Such devices are not effective for many corrosion management applications such as in controlling and detecting the addition of corrosion inhibitors introduced in pipeline fluids.

Attempts have been made to increase the sensitivity and improve the resolution of measurements to the changes in the resistance of the element due to corrosion and/or erosion of the element in electrical resistance corrosion monitors. However, the sensitivity in such corrosion monitors is typically limited to several days before corrosion can be measured. For example, European Patent Application No. 84303370.5 discloses a flush mounting electrical resistance corrosion probe that has a sample element and a reference element where the reference element is shielded from the corrosive fluid environment by the sample element and an insulating material plug of the probe. Although the reference element is responsive to the temperature conditions of the environment in such a configured probe, the reference element and the sample element may not be at substantially identical temperatures during corrosion monitoring. Since the reference element is protected from the fluid environment by the sample element and electrically insulating material of the plug that has low thermal conductivity, the temperature and resistance of the reference element changes more slowly than the temperature of the sample element. Even slow temperature changes producing small temperature differences between the sample element and the reference element may produce significant changes in the resistance ratio. Additionally, the elements are formed in a manner that the values of temperature coefficients of resistivity for each element may differ. Consequently, these factors limit the sensitivity of such a configured probe and can yield spurious indications of corrosion when the temperature of the fluid environment is changing or even when the temperature of the fluid is constant as the temperature in the probe may differ from the fluid environment temperature.

Therefore, there is a need for an electrical resistance corrosion monitor with a greater sensitivity to accurately measure at a higher resolution, for example in minutes or hours, the corrosion and/or erosion of a material in a corrosive/erosive environment where the environment temperature may be fluctuating.

SUMMARY OF THE INVENTION

An object of the present invention is to provide an apparatus with improved sensitivity for monitoring change in the thickness of an element.

The present invention provides a probe device for use in an apparatus for monitoring changes in the resistance of an element caused by a fluid at the surface thereof, said probe device comprising a first element having a surface that is directly accessible. by a fluid, a second element electrically connected in series with said first element and forming therewith a path For the passage of electrical current to flow therethrough, wherein said first element and said second element are formed from the same piece of material, said piece of material being divided along an elongate slot to form a boundary of said first element on one side of said slot and a boundary of said second element on the other side of said slot.

BRIEF DESCRIPTION OF THE DRAWINGS

Examples of embodiments of the present invention will now be described with reference to the drawings in which.

DESCRIPTION OF THE PREFERRED EMBODIMENTS

Figure 1:
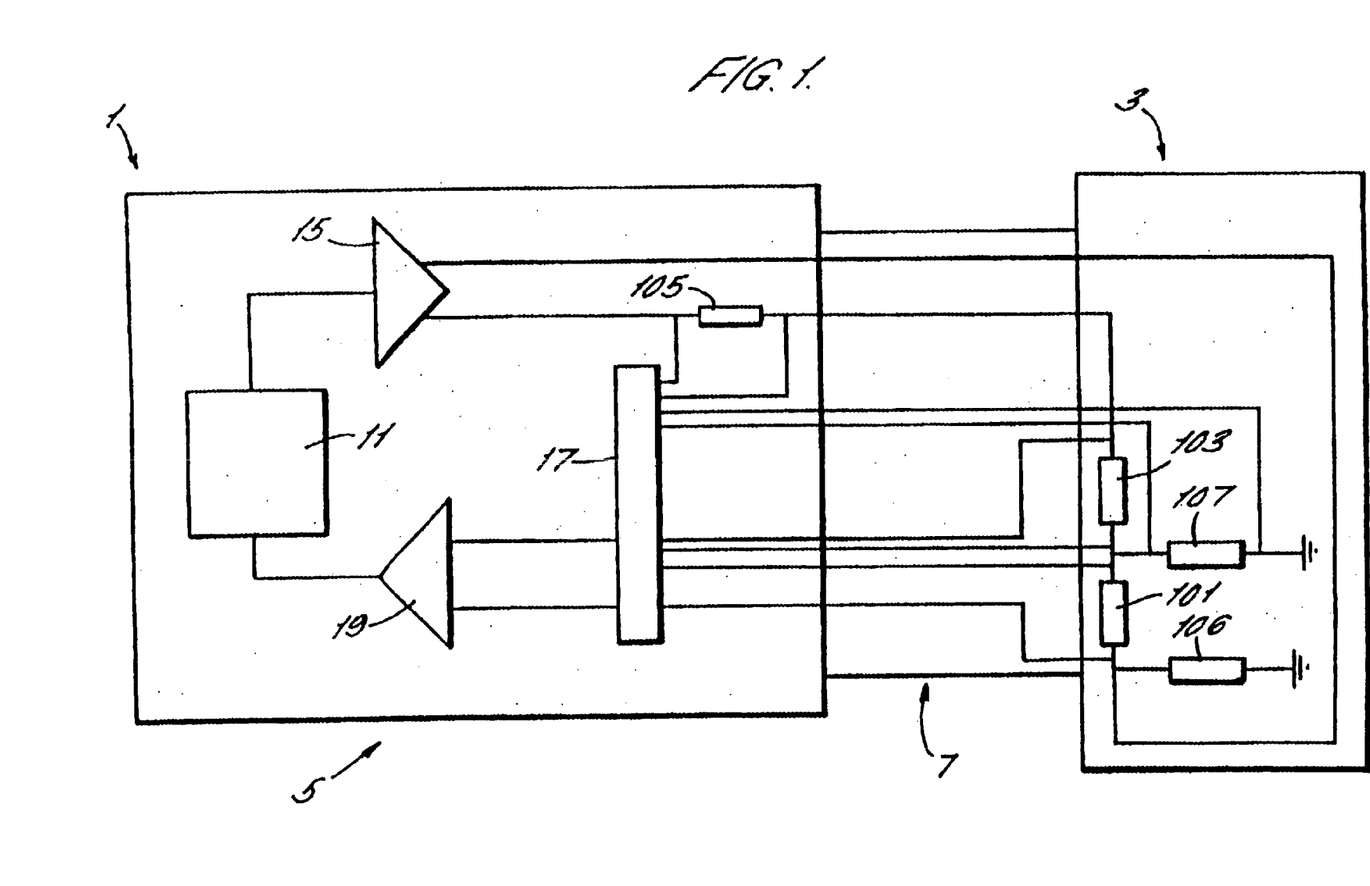
FIG. 1 shows a block circuit diagram of an embodiment of the present invention.

Referring to FIG. 1, an apparatus, such as a corrosion monitor 1, for monitoring changes in the resistance of an exposed element 101 generally comprises a probe device 3 comprising the exposed element 101 and a reference element 103, electronic circuitry 5 and a cable 7 for connecting the electronic circuitry to the probe.

The exposed element and the reference element are electrically connected in series and connected to a current generator 11,15 which drives current through the series circuit. The electronic circuitry further comprises voltage monitoring means 11,19 arranged to monitor the voltage developed across each of the exposed and reference elements. In a preferred embodiment, the electronic circuitry further includes a multiplexer 17 for switching the voltage monitoring means to measure alternately the voltage across each element.

Figure 2:
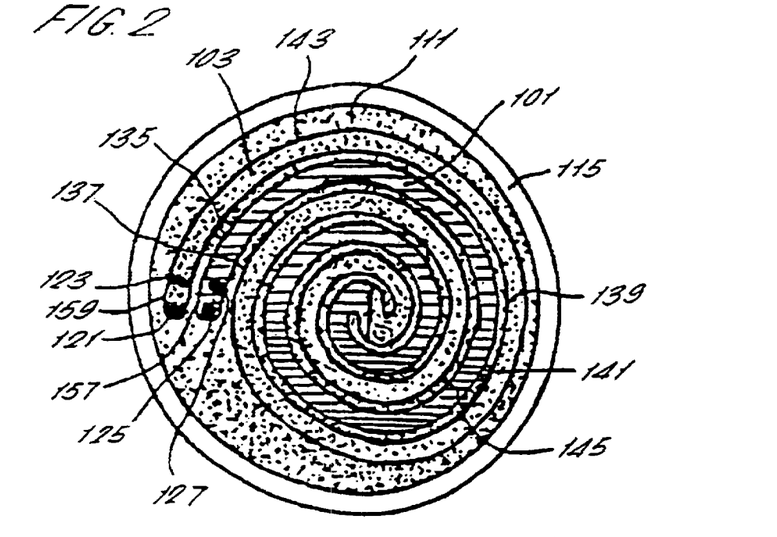
FIG. 2 shows an elevation view of a double spiral probe.
Figure 3:
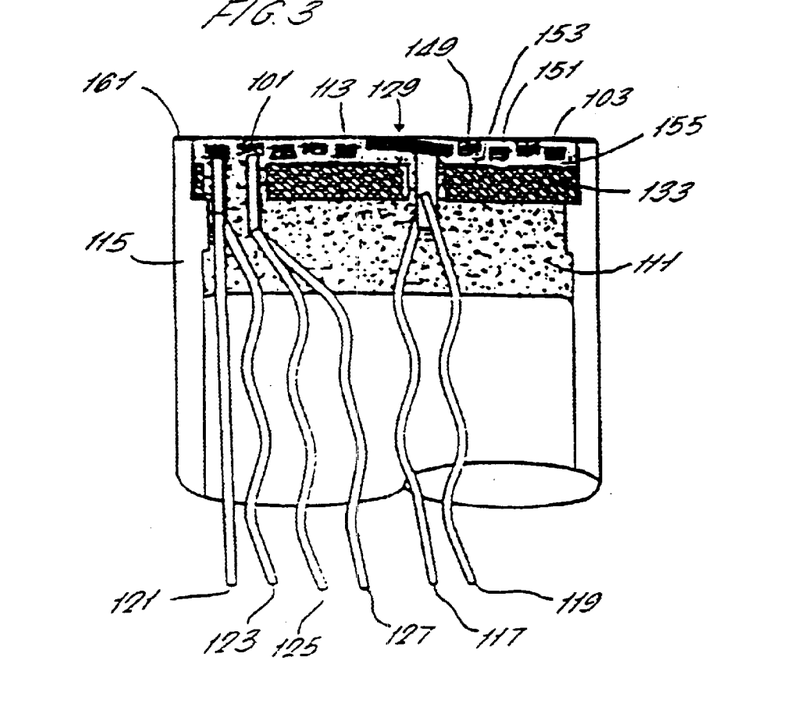
FIG. 3 shows a side cross-sectional view of the probe shown in FIG. 2.

FIGS. 2 to 7 show the probe 5 with configurations of the probe elements. In FIGS. 2 and 3, a double spiral probe is shown and in FIGS. 4 to 7 protruding probes are shown. The elements of the probe are situated proximate to each other to help ensure that the temperature difference between the exposed element and reference element is minimal and the reference element has good thermal contact with the environment, such as the fluid in the pipeline. Even if the environment temperature, of the pipeline fluid for example, is constant, the exposed and reference elements are unlikely to be at the same temperature in the prior art configurations. As the exposed element is in contact with the pipeline fluid and the reference element is not in contact with the pipeline fluid, the temperature of the reference element may be affected by the surrounding environment, i.e., the probe body and the electrical leads. Unlike the prior art, the insulating material protecting the reference element in the probe is as thin as possible and the space between reference element and exposed element is also minimised to help ensure that the reference element and exposed element are at substantially identical temperatures. In the prior art, the reference element is in poor thermal contact because the reference element is protected from the environment by at least a few millimetres of insulating material. To ensure that any inhomogeneity that may be present in the metal itself and resulting from the machining process, both elements may be machined from the same piece of metal such that a narrow slit defines the two elements. In this manner, any inhomogeneities in the metal (which could effect the temperature coefficient of resistivity of the metal) either inherent in the metal arising from machining or from subsequent annealing and the like, are shared by both the exposed element and the reference element and are common to both so that their effects are substantially cancelled. In this manner, the temperature coefficient of resistivities in both probe elements are as closely matched as possible. Matching the temperature coefficient of resistivities in each element as closely as possible is important because as discussed above the exact metallurgical characteristics of samples of steel may, even from the same piece of metal, vary, for example in the range of 200 ppm ° $C.^{-1}$ to 500 ppm ° $C.^{-1}$. If the probe elements exhibit different temperature coefficient of resistivities, false indications corrosion may result. To illustrate this, even if the temperature coefficient of resistivities for probe elements differ by 10 ppm ° $C.^{-1}$, a change in temperature of 50° C. would change the resistance ratio of 500 ppm. Therefore, unlike the prior art, not only are the probe elements machined from the same piece of material, the elements are defined by a narrow slit made in the material so that the elements exhibit temperature coefficient of resistivities as near to identical as possible. Additionally, since the temperature coefficient of resistivity of steel may cause an inaccurate reading of change in resistance ratio between the exposed element and the reference element, it is important that the temperature difference between the two elements is as small as possible. For example, a 0.05° C. temperature difference could change the measured resistance by 20 ppm which would result in spurious indications of corrosion and/or erosion.

In FIGS. 2 and 3, a flush double spiral probe 3 is shown for mounting flush with the wall of a pipe in a pipeline. The flush double spiral probe comprises a steel double spiral consisting of the exposed element 101 and the reference element 103 of the probe. The double spiral is preferably of a similar material as that of the material to be monitored, for example the metal material of a steel pipeline. The double spiral is formed from a metal disk with a thickness of, for example, between 0.1 mm to 6 mm, although other thicknesses may also be used. The metal disk is divided along an elongate slot or slit to form the exposed and reference elements. The process by which the material s divided is preferably chosen so as to minimise any changes in the microstructure of the material both local to and remote from slot, and may for example include spark machining, wire corrosion, etching and the like. In this embodiment, two spiral narrow slits 135 and 137 are formed in the disk to define the exposed element and the reference element. The slits 135 and 137 are preferably narrow, for example in the range of 0.2 mm–4 mm, however the slits should be wide enough for the insulating material to flow and fill the gaps between the elements during manufacture of the probe. The first slit 135 defines the inner edge 139 of the reference element 105 and the outer edge 141 of the exposed element 101, and the second slit 137 defines the outer edge 143 of the reference element and the inner edge 145 of the exposed element. Advantageously, with this configuration the reference element is depicted as the outermost element and the exposed element is the innermost element to maximise the distance from the exposed element from the housing 115 to help prevent "bridging" caused by electrically conductive contaminants in the fluid that may lodge between the exposed element and the housing on the probe which may cause spurious values of exposed element resistance. Other arrangements of the elements instead of the circular spiral configuration may be configured such as oval or rectangular and the like. In this configuration, the exposed element 101 is 60% shorter than the reference element 103. The widths of the two elements may be the same, as shown, although in other embodiments, the widths of the elements may differ. Of course, the number of spirals shown may be increased or decreased accordingly. If the exposed element is too narrow, the resistance of the exposed element is more prone to the effects of pitting, i.e., localized corrosion, which may result in erroneous readings and shortens the life span of the probe. Additionally, to provide a better signal to noise ratio, the reference element preferably has a greater resistance than the initial resistance of the exposed element prior to use of the probe. Preferably, the resistance of the reference element is about twice that of the exposed element prior to use. Conveniently, with this configuration, the probe should be replaced once the resistance of the exposed element has increased, due to the loss of metal by corrosion and erosion by the fluid environment, to equal the resistance of the reference element. Prolonging the life of the probe beyond this point may result in inaccurate readings due to non uniform corrosion and erosion which typically occurs in thinner elements as discussed above.

The double spiral is mounted in the probe housing 115 such that the front surface 151 of the reference element is recessed with respect to the plane of the front surface 149 of the exposed element. The front surface 151 of the reference element may be recessed a number of ways, for example by either bending the double spiral at the mid-point Joining spar 129 to recess the reference element portion of the double spiral or by physically removing material, by for example spark machining, the front surface 151 of the reference element portion of the double spiral, which may be either before or after machining the slits in the disk. If material from the surface of the reference element is removed, then the back surface 155 of the reference element is in the same plane as the back surface 153 of the exposed element. Current leads and voltage leads are joined to the double spiral. Current lead 121 is connected to reference element end 159 and current lead 125 is connected to exposed element end 157. Common voltage leads 117 and 119 are connected to and make separate electrical contact to the central spar region 129 of the double spiral, while reference element voltage lead 123 and exposed element voltage lead 127 are connected closely with the current leads 121 and 125 to the reference element end 159 and exposed element end 157 of the double spiral, respectively.

The double spiral is mounted in the probe housing 115 with an insulating material, e.g. epoxy resin or ceramic or the like, to bond the double spiral to a backplate 133. Conveniently, the backplate is preferably a metal with a high thermal conductivity such as copper and the like to improve thermal contact of the back surfaces 153 and 155 of the elements with the pipeline fluid temperature. With this configuration, the difference in temperature between two elements resulting from the higher thermal impedance to the fluid experienced by the reference element because of the thin protective layer is partially compensated for by the backplate. A thin layer of insulating material, preferably in the range of 0.1 mm to 1 mm, is used to bond the probe elements to the back plate. Conveniently, if the reference element is recessed by bending, the back surface 155 of the reference material may be closer to the back plate. Such a configuration substantially minimises the thermal impedance between the reference element and back plate which helps compensate for the higher thermal impedance between the front surface 151 of the reference element and the pipeline fluid.

The insulating material is formed flush with the end 161 of the probe housing and the front surface 149 of the exposed element 101 to provide a thin protective layer 113 of insulating material over the front surface 151 of the reference element 103. Preferably, the protective layer is a 0.2 mm layer of insulating material which is thinner than the protective layer in the prior art and therefore the thermal contact in which the reference element is in with the fluid environment is improved. The insulating layer covers the front surface 151 of the reference element 103, however any depth of insulating material may coat the reference element as long as the reference element remains in good thermal contact with the fluid environment.

In any embodiment of the probe, the thin protective covering, e.g. 113, may be a non-corrosive metallic cover layer. The metallic cover layer may for example comprise gold, platinum, or chromium or any other relatively inert metal or other metal which does not corrode to any significant degree when exposed to the fluid in question. Providing a non-corrosive metallic cover layer 113 over the reference element 103 provides the advantage of providing the reference element with good thermal contact with the pipeline fluid. Preferably, the metallic layer is relatively than such that it does not significantly modify the resistance of current path provided by the reference element as a whole.

Figures 4, 5:
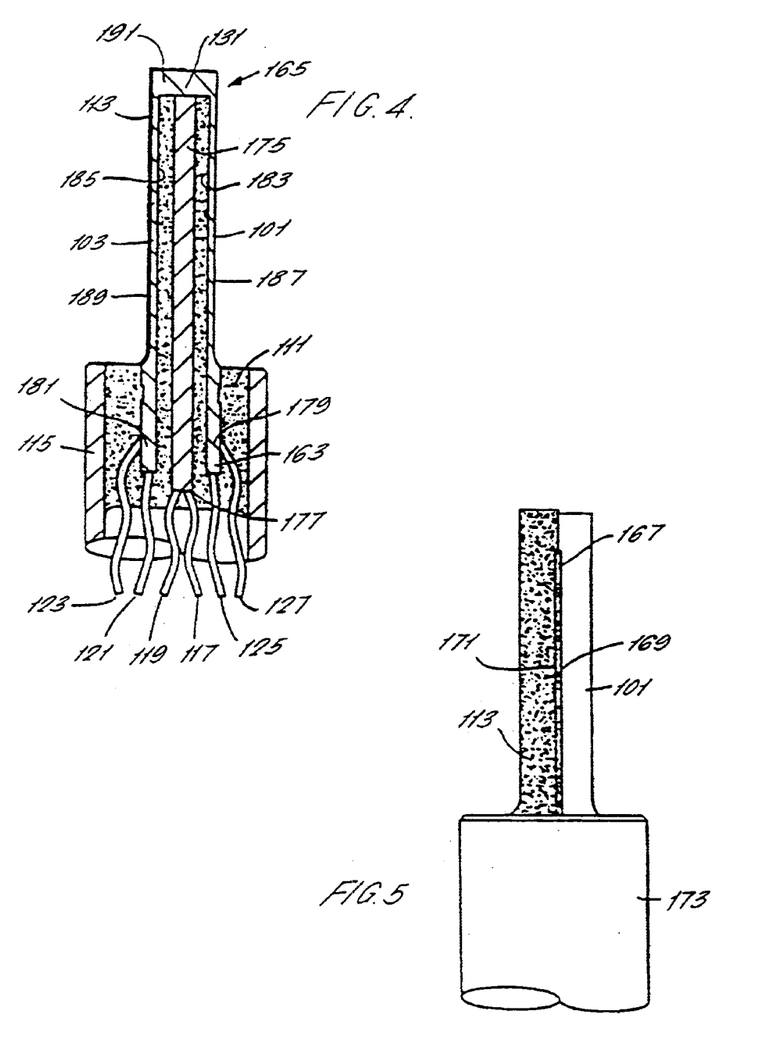
FIG. 4 shows a side cross-sectional view of a split tube protruding probe.
FIG. 5 shows a side elevation view of the probe shown in FIG. 4.

In FIGS. 4 and 5, a split tube protruding probe is shown for mounting in a wall of a pipe and protruding into the fluid environment in the pipeline. The split tube protruding probe comprises a split tube consisting of the exposed element 101 and the reference element 103. The split tube is of the same metallic material as that of the pipeline, e.g. steel, and is machined from a metal rod. The rod is centrally drilled from one end 163 of the rod along the longitudinal axis of rod to 5 mm to 10 mm from the other end 165 or the rod to form a thin walled tube with a bridge 131 at one end 165. The thickness of the tube walls is preferably in the range 0.1 mm to 6 mm. The tube may be spark machined to form the probe elements 101 and 103. Two slits (only one slit is shown, slit 167) are formed along the longitudinal axis of the tube section up to the bridge 131 to define the exposed element 101 and the reference element 103. The slits may be as narrow as discussed above, however, for this embodiment the slits may be wider than for other embodiments. The narrow slits define the edges (only edges 169 and 171 are shown) of each probe element.

The split tube is mounted to a steel flange 173 with a suitable seal such as epoxy resin or ceramic or the like. A coaxial metal rod 175 is joined, for example by welding, to the bridge and extending in the tube just beyond the end 163 of the tube. The coaxial metal rod may share the same purposes as the back plate as discussed above in the flush double spiral probe embodiment. For example, the coaxial metal rod is preferably a metal of high thermal conductivity such as copper and the like to improve thermal contact of the back surfaces of the probe elements with the pipeline fluid and help maintain the two elements at near identical temperature as possible. The coaxial metal rod 175 also strengthens the structural integrity of the split tube protruding probe. Current lead 121 is connected to reference element end 181 and current lead 125 is connected to exposed element end 179. Common voltage leads 117 and 119 are connected to end 177 of coaxial metal rod 175, while voltage leads 123 and 127 are connected closely with the current leads 121 and 125 to the reference element end 181 and the exposed element end 179, respectively.

The split tube is filled with a suitable insulating material, e.g. epoxy resin or ceramic or the like, to protect the inner surfaces 183 and 185 of the probe elements from the fluid environment in the pipeline. To protect the reference element 103, the outer surface 189 of the reference element and reference element portion of the bridge 191 is thinly covered by preferably 0.2 mm layer of insulating material as discussed above in the flush double spiral probe embodiment. The outer surface 187 of the exposed element and the exposed element portion of the bridge are left uncovered.

Figures 6, 7:
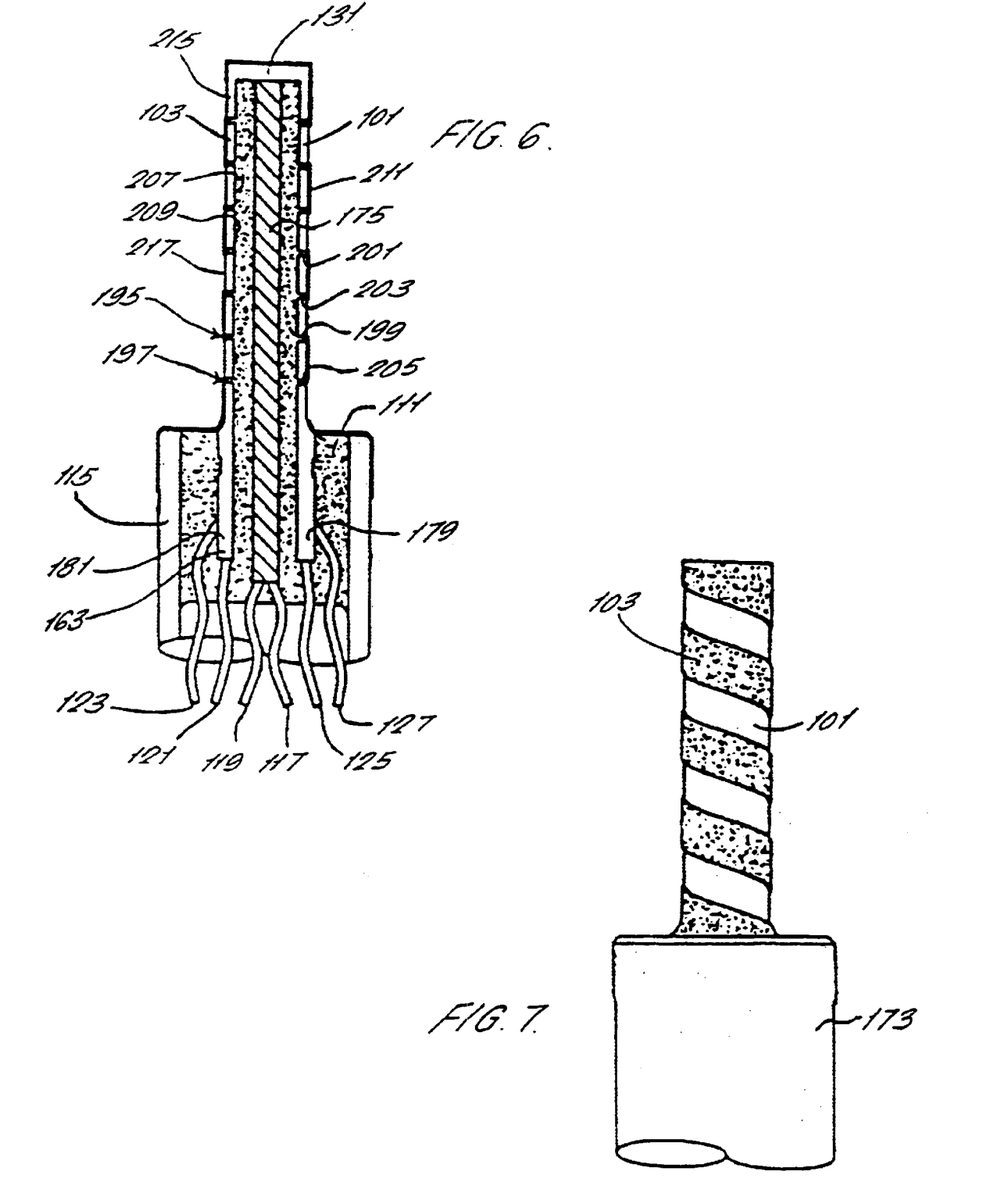
FIG. 6 shows a side cross-sectional view of a double helix protruding probe.
FIG. 7 shows a side elevation view of the probe shown in FIG. 6.

In FIGS. 6 and 7, a double helix protruding probe is shown which is similar to the split tube protruding probe discussed above. The double helix protruding probe comprises the tube as machined above for the split tube protruding probe, but the exposed element 101 and the reference element 103 are each helical strips defined by two helical narrow slits 195 and 197 formed along the longitudinal axis of the tube. The two helical narrow slits are machined into the tube to form the probe elements. For this embodiment, the slits may be as narrow as discussed above however preferably the slits are 1 mm. The first slit 195 defines the lower edge 199 of the exposed element 101 and the upper edge 201 of the reference element, while the second slit 197 defines the upper edge 203 of the exposed element and the lower edge 205 of the reference element.

As with the split tube protruding probe, the elements are mounted to a steel flange 173 with a suitable seal such as epoxy resin or ceramic or the like. A coaxial metal rod 175 serve the similar purposes of the back plate as discussed above in the flush double spiral probe embodiment and the coaxial metal road as discussed in the split tube protruding probe embodiment. The coaxial metal rod may also be preferably a metal of high thermal conductivity such as copper and the like to improve thermal:al contact of the back surfaces of the probe elements with the pipeline fluid and help maintain the two elements at near identical temperature as possible. The coaxial metal rod is also joined to the bridge and extends in the tube just beyond the end 163 of the tube which also strengthens the structural integrity of the double helix protruding probe. Current lead 121 is connected to reference element end 181 and current lead 125 is connected to exposed element end 179. Common voltage leads 117 and 119 are connected to end 177 of coaxial metal rod 175, while voltage leads 123 and 127 are connected closely with current leads 121 and 125 to the reference element end 181 and the exposed element 179, respectively. The split tube is also filled with a suitable insulating material, e.g. epoxy resin or ceramic or the like, to protect the inner surfaces 207 and 209 of the probe elements. To protect the reference element 103, the outer surface 211 of the reference element and reference element portion 213 of the bridge is thinly covered by the insulating material by preferably a 0.2 mm layer as discussed above in the flush double spiral probe embodiment. The outer surface 217 of the exposed element and the exposed element portion 215 of the bridge are left uncovered.

The double helix protruding probe, like the split tube protruding probe, compensates for any axial variations in the temperature coefficient of resistivity of the tube. The double helix protruding probe also compensates for any circumferential variations in she temperature coefficient of resistivity of the tube. Additionally, in the double helix protruding probe having a tube of the same length and wail thickness, the resistance of the elements is higher than the resistance of the elements in the split tube protruding probe. As discussed above, increasing the resistance of the exposed element increases the sensitivity of the probe by improving resolution of the measurements to the changes in resistance of the exposed element due to corrosion and/or erosion by the fluid pipeline. For example, for a 10 mm diameter probe with slits machined to form 3 mm wide probe elements, the resistance of the double helix protruding probe is approximately 28 times higher than the resistance of the split tube protruding probe. Similarly, for 5 mm wide elements, the resistance for the helix protruding probe is approximately 10 times higher then that of the split tube protruding probe.

Advantageously, in any of the embodiments, the corrosion monitor may be configured to monitor temperature of the probe. A third resistive element, a calibration resistor 105, may be included in the electronic circuitry 5 as shown in FIG. 1. Such a calibration resistor provides for monitoring the temperature of the probe, and hence the temperature of the pipeline fluid, without the need for special temperature sensors as in conventional corrosion probes. In FIG. 1, the calibration resistor 105 may be included in the electronic circuitry 5 in series with the exposed element 101 and the reference element 103. En a preferred embodiment a switch, such as multiplexer 17, may connect separate voltage terminals for each of the exposed element 101, reference element 103, and calibration resistor 105 to the voltage monitoring means 11, 19.

The calibration resistor 105 allows the accurate measurement of the reference element temperature without the need for additional temperature sensors. The absolute resistance of the reference element 103 is determined with the equation $Rr=(Vr/Vc)Rc$, where $Rr$ is the resistance of the reference element, $Vr$ is the voltage across the reference element, $Vc$ is the voltage across the calibration resistor and $Rc$ is the resistance of the calibration resistor. Since the relationship between resistance and temperature is near linear, simply a linear interpolation between calibration points is adequate, however, the calibration procedure of the probe may involve a look-up table comprising values of $Rr$ recorded at various known temperatures during a calibration procedure to determine the real-time temperature for resistance $Rr$. This provides an accurate value for the temperature of the reference element and provides an indication of the temperature of the pipeline fluid. Such a look up table may be stored in a memory (not shown) in the electronic circuitry 5.

The calibration resistor is preferably highly stable and insensitive to temperature fluctuations with a resistance which is preferably similar to that of the probe elements. The calibration resistor preferably also has a low temperature coefficient of resistance (e.g. ±10 ppm ° $C.^{-1}$) and a low inductance. Alternatively, if a resistor having the above coefficient of resistance is nor available the error may be corrected by measuring the temperature of the calibration resistor directly in the electronic circuitry and determining its actual resistance From its known temperature coefficient of resistance. The use of a metallic, non-corrosive cover layer on the reference element, is particularly advantageous when measuring temperature, since the metallic layer would generally have a high thermal conductivity and could be relatively thin so that the temperature of the reference element closely follows the temperature of the fluid.

Conveniently, in any of the embodiments, the corrosion monitor may be configured to monitor the electrical conductivity of the pipeline fluid. In the corrosion monitor, a voltage $V_A$, which is monitored in the corrosion probe 3, is developed across the exposed element 101 when the current generator 11,15 drives a current through the exposed element 101. If the pipeline fluid is conducting, for example a pipeline fluid such as oil may contain traces of water, a leakage current $I_L$ may flow from the exposed element 101 through the conductive fluid, e.g. water, to the body of the probe 115. This may occur for example in the flush double spiral probe 3 shown in FIGS. 2 and 3 where the distance between the outer limb of the exposed element 101 and the probe body 115 may be relatively small.

In FIG. 1, a pipeline fluid conductivity measurement resistor 107 is provided. In the probe, the point where probe elements 101, 103 are connected is not electrically connected directly to the probe body 115. Instead, the conductivity measurement resistor 107 is electrically connected where the probe elements 101, 103 are electrically connected, e.g. the central spar region 129 of the double spiral in FIG. 2, and to ground. The conductivity measurement resistor 107 Preferably has a finite resistance $R_M$, for example 10 kΩ to 1 MΩ, and is connected to ground. The leakage current I, flowing through the conductivity measurement resistor 107 develops a voltage $I_L R_M$ which is measured by voltage monitoring means 11, 19. In a preferred embodiment a switch, such as multiplexer 17, may connect the voltage terminals for the conductivity measurement resistor 107 to the voltage monitoring means 11, 19.

The conductivity measurement resistor 107 allows the accurate measurement of electrical conductivity of the pipeline fluid. The leakage current flows from the outside turn of the exposed element 101 spiral to the probe body. The average voltage developed along the outside turn is a fraction f of the voltage $V_A$ produced by the current driven by the current generator 11, 15 through the exposed element 101. The values of this fraction may depend on several factors including the geometry of the exposed element 101 and is generally On the range of 0.1 to 0.5.

The conductivity of the pipeline fluid is determined by the equivalent resistance of the pipeline fluid, i.e. the resistance of the fluid from the outer limb of the exposed element 101 to the probe body 115. The conductivity of the pipeline fluid may be determined from the resistance of the pipeline fluid with calibration in fluids of known electrical conductivity. Thus, the equivalent resistance of the pipeline fluid is determined with the equation $R_L = R_M(1 + fV_A/V_M)$, where $V_M/R_M = fV_A/(R_M + R_L)$, since $I_L = fV_A/(R_M + R_L)$ and $V_M = I_L R_M$, and where $R_L$ 106 represents the equivalent resistance of the pipeline fluid and is represented in FIG. 1.

In this configuration, the conductivity of the pipeline fluid may be monitored in real-time. This is useful for determining for example the water content of a pipeline fluid such as oil. Thus, the higher the water content the higher the conductivity of the pipeline fluid. Monitoring the conductivity of the pipeline fluid is also useful for monitoring the addition of corrosive inhibitors to the pipeline fluid. The conductivity of the pipeline fluid may provide a measure of the corrosiveness of the fluid and could be used as part an advance warning system in predicting pipeline corrosion so that appropriate preventative action can be taken.

Further modifications to the embodiments described herein will be apparent to those skilled in the art.

What is claimed is:

1. A probe device for use in an apparatus for monitoring changes in the resistance of an element caused by a fluid at the surface thereof, said probe device comprising a first element having a surface that is directly accessible by a fluid, a second element, which is a reference element, electrically connected in series with said first element and forming therewith a path for the passage of electrical current to flow therethrough, wherein said first element and said second element comprise a single piece of material having an elongate slot to forming a boundary of said first element on one side of said slot and a boundary of said second element on the other side of said slot.

2. A probe device as claimed in claim 1, wherein each of said first and second elements are formed as strips from said piece of material.

3. A probe device as claimed in claim 1, wherein a locus of said slot extends about an axis.

4. A probe device as claimed in claim 1, wherein said first and second elements are defined by first and second spiral slots formed in said piece of material such that each slot defines both an edge of said first element on one side thereof and an edge of said second element on the other side thereof.

5. A probe device as claimed in claim 4, wherein said first and second elements are electrically connected at a position at or near the centre of their respective spirals.

6. A probe device as claimed in claim 1, further comprising a layer of material over said second element for preventing contact between a fluid and said second element.

7. A probe device as claimed claim 6, further comprising a metal member disposed adjacent the surface of said second element which, in use, faces away from said fluid, to increase the thermal coupling between said fluid and said second element.

8. A probe device as claimed in claim 7, comprising a layer of material over said second element for preventing contact between fluid and said second element and wherein said metal member is closer to said second element than to said first element.

9. A probe device as claimed in claim 1, wherein said piece of material comprises an elongate member and said first and said second elements are defined by said slot extending longitudinally in said member.

10. A probe device as claimed in claim 9, wherein said member comprises a tubular member and said first and second elements are defined by first and second slots extending linearly and substantially parallel to the longitudinal axis of said tubular member.

11. A probe device as claimed in claim 9, arranged in a flow of fluid, wherein said second element has a surface that is accessible by said fluid, said slot being arranged such that the surface of said first element that is accessible by said fluid is directed into the flow of fluid and the surface of said second element that is accessible by said fluid is directed substantially away from said flow.

12. A probe device as claimed in claim 9, wherein said member comprises a tubular member and said first and said second elements are defined by first and second helical slots extending around the longitudinal axis of said tubular member.

13. A probe device as claimed in claim 9, further comprising a layer of material over said second element for preventing contact between a fluid and said second element.

14. A probe device as claimed in claim 9, wherein said first element is electrically connected to said second element at a point adjacent one end of said elongate member.

15. A probe device as claimed in claim 9, further including a metal member mounted within and extending along said tubular member.

16. A probe device as claimed in claim 15, wherein said metal member is electrically connected to both said first and second elements at a point adjacent or at the end of said tubular member.

17. A probe device claimed in claim 16, wherein said metal member is disposed adjacent said element to increase the thermal coupling between said fluid and said second element.

18. A probe device as claimed in claim 1, wherein said second element has an electrical resistance that is greater than that of said first element along said path.

19. A probe device as claimed in claim 1 in combination with an apparatus for monitoring changes in the resistance of said first element caused by a fluid at the surface thereof, said apparatus comprising driving means for generating a current and driving said current through said first and second elements and monitoring means arranged to monitor the respective voltages across said first and second elements.

* * * * *

UNITED STATES PATENT AND TRADEMARK OFFICE
CERTIFICATE OF CORRECTION

PATENT NO.    : 6,693,445 B1
DATED         : February 17, 2004
INVENTOR(S)   : John Sutton It is certified that error appears in the above-identified patent and that said Letters Patent is hereby corrected as shown below:

Column 10,
Line 17, after the word "slot" delete "to".

Signed and Sealed this

Twenty-second Day of November, 2005

JON W. DUDAS
*Director of the United States Patent and Trademark Office*